United States Patent [19]

Sato et al.

[11] 4,284,571
[45] Aug. 18, 1981

[54] PROCESS FOR PRODUCING PHTHALIC ANHYDRIDE AND CATALYST THEREFOR

[75] Inventors: Takahisa Sato; Yoshiyuki Nakanishi; Keizo Maruyama, all of Himeji; Takehiko Suzuki, Ohtsu, all of Japan

[73] Assignee: Nippon Shokubai Kagaku Kogyo Co. Ltd., Osaka, Japan

[21] Appl. No.: 97,982

[22] Filed: Nov. 28, 1979

[30] Foreign Application Priority Data

Nov. 29, 1978 [JP] Japan ................................. 53/146459

[51] Int. Cl.$^3$ ........................................... C07D 307/89
[52] U.S. Cl. ................................... 260/346.4; 252/435
[58] Field of Search ..................................... 260/346.4

[56] References Cited

U.S. PATENT DOCUMENTS

| 3,296,281 | 10/1965 | Hughes | 260/346.4 |
| 3,296,846 | 12/1965 | Ono et al. | 252/435 |
| 4,046,780 | 9/1977 | Nakanishi et al. | 260/346.4 |

FOREIGN PATENT DOCUMENTS

| 2238067 | 2/1974 | Fed. Rep. of Germany . |
| 2309657 | 9/1974 | Fed. Rep. of Germany . |
| 2417145 | 10/1974 | Fed. Rep. of Germany . |
| 2330841 | 1/1975 | Fed. Rep. of Germany . |
| 2436009 | 2/1976 | Fed. Rep. of Germany . |

OTHER PUBLICATIONS

Zimmer, Chemical Engineering (Mar. 1975), pp. 82 & 83.

Hellmer et al., I. Chem. E. Symposium Series, vol. 50 (1976), pp. 4–16.

*Primary Examiner*—Richard Raymond
*Attorney, Agent, or Firm*—Sherman & Shalloway

[57] ABSTRACT

A process for producing phthalic anhydride, which comprises packing a catalyst into a multitube fixed bed converter, said catalyst comprising a catalytically active material composed of 1 to 20 parts by weight as $V_2O_5$ of vanadium oxide, 99 to 80 parts by weight of anatase-type titanium oxide being porous and having a particle diameter substantially of 0.4 to 0.7 micron and a specific surface area of 10 to 60 m$^2$/g, and per 100 parts by weight of the sum of said two components, 0.01 to 1 part by weight as $Nb_2O_5$ of niobium oxide, 0.05 to 1.2 parts by weight as an oxide of at least one ingredient selected from the group consisting of potassium, cesium, rubidium and thallium, and 0.2 to 1.2 parts by weight as $P_2O_5$ of phosphorus, and a porous carrier having an alumina content of not more than 10% by weight, a silicon carbide content of at least 80% by weight and an apparent porosity of at least 10% supporting said catalytically active material thereon, wherein the total volume of pores having a diameter of 0.15 to 0.45 micron present in the layer of the catalytically active material on the carrier is at least 50% of that of pores having a diameter of not more than 10 microns present in said layer of the catalytically active material; and passing o-xylene or naphthalene and oxygen or a molecular oxygen-containing gas through the catalyst layer at a temperature of 300° to 450° C., thereby catalytically oxidizing the o-xylene or naphthalene; and a catalyst suitable for performing said process.

15 Claims, No Drawings

PROCESS FOR PRODUCING PHTHALIC ANHYDRIDE AND CATALYST THEREFOR

This invention relates to a process for producing phthalic anhydride by the catalytic vapor-phase oxidation of o-xylene or naphthalene with a gas containing molecular oxygen. More specifically, it relates to a process for producing phthalic anhydride by the catalytic vapor-phase oxidation of a molecular oxygen-containing gas containing o-xylene or naphthalene in a high concentration, and to a catalyst suitable for performing this process.

According to this invention, there are provided a process for producing phthalic anhydride stably with high productivity by the catalytic vapor-phase oxidation of a molecular oxygen-containing gas containing o-xylene or naphthalene in a high concentration of, for example, more than 60 g/Nm$^3$ in the presence of a catalyst containing vanadium oxide while avoiding a danger of explosion both at a gas inlet and a gas outlet of a converter; and a catalyst suitable for the process.

Phthalic anhydride has been produced previously by the catalytic vapor-phase oxidation of o-xylene or naphthalane using air as a molecular oxygen-containing gas. To avoid the danger of explosion, it is usual in the conventional method to maintain the concentration of the starting gas below the lower limit of explosion during the reaction. For example, in the production of phthalic anhydride from o-xylene, the concentration of the starting gas should be maintained at below 40 g/Nm$^3$. With technological advances made in the selectivity and heat resistance of the catalyst and in reaction engineering, operations within an explosive range have been attempted for the past several years to increase productivity per unit converter and save energy. According to these operations, the concentration of o-xylene in the air is increased to more than 40 g/Nm$^3$ in the aforesaid catalytic vapor-phase oxidation process. Suggestions relating to such a process are disclosed in Japanese Laid-Open Patent Publications Nos. 40539/75 (West German Laid-Open Patent Publication No. 2,417,145), 4051/75 (West German Laid-Open Publication No. 2,330,841), and 134618/74 (West German Laid-Open Publication No. 2,309,657).

The actual operation of these high gas concentration processes involves using an o-xylene/air ratio of at most 60 g/Nm$^3$, as is described in detail in Chemical Engineering (March 1974, page 82), and I. Chem. E. Symposium Series (1976, Vol. 50, p. 4). The reason for this is not entirely clear, but presumably the purpose of it is to keep the composition of the product gas from the outlet of the converter outside the explosive range. The composition of the starting gas at its inlet portion is within the explosive range. But as described in U.S. Pat. No. 3,296,281, by increasing the linear velocity of the gas between the material charging section and the catalyst layer in the converter, the danger of explosion can be avoided at a gas concentration of up to a certain point even if the gas composition in the stationary state is within the explosive range. After the gas has left the gas outlet of the converter, however, it is impossible, in view of the operation of recovering the resulting phthalic anhydride, to narrow the apparent explosive range of the gas composition by increasing the linear velocity of the gas.

It may be taken for granted that the oxidation reaction at an increased concentration of the starting gas is safer than ordinary operations outside the explosive range, because the concentration of residual oxygen in the product gas decreases. This applies, however, to an o-xylene/air ratio of up to about 60 g/Nm$^3$, and it is difficult to apply this principle to higher gas concentrations. When the reaction is carried out simply at an increased o-xylene/air concentration of more than 60 g/Nm$^3$, the concentration of residual oxygen necessarily decreases further. But since the concentrations of combustible phthalic anhydride, maleic anhydride, carbon monoxide, etc. increase, the composition of the product gas falls within the explosive range.

Another possible reason for this is the restriction in regard to the performance of catalyst, as described in I. Chem. E. Sym. Series (1976, Vol. 50, p. 4). The catalytic vapor-phase oxidation of o-xylene to form phthalic anhydride is very exothermic. When the concentration of the gas is increased abnormal heat generation called "hot spot" is liable to occur locally in the catalyst layer. This induces excessive oxidation reaction, which results in a decrease in the yield of phthalic anhydride and in a marked degradation of the catalyst at the hot spot sites. It has been found that when o-xylene is catalytically oxidized with air in the vapor phase at a concentration of 80 g/Nm$^3$ using catalysts described, for example, in Japanese Patent Publication No. 41271/74 (U.S. Pat. No. 3,926,846), and Japanese Laid-Open Patent Publications No. 42096/76 (West German Laid-Open Patent Publication No. 2,238,067) and 49189/76 (West German Laid-Open Patent Publication No. 2,436,009), for example the catalyst described in Japanese Patent Publication No. 41271/74, the temperature of the hot spots exceeds 500° C., and side-reactions to form maleic anhydride, benzoic acid, carbon dioxide, etc. increase, and the yield of phthalic anhydride cannot reach 100% by weight. It is difficult therefore to obtain phthalic anhydride in a high yield even when the ratio of o-xylene/air is simply increased to more than 60 g/Nm$^3$ in a conventional known conventional method in using a known conventional catalyst.

The present inventors searched for reaction conditions under which the temperature of hot spots is low and side-reactions are reduced even at a high gas concentration, and suitable catalysts for achieving these reaction conditions. As a result, they found that the composition of the gas in the reaction system can be always maintained outside the explosive range by recycling a part of the exhaust gas left after the recovery of phthalic anhydride to a converter for reuse. They succeeded in developing a process capable of affording phthalic anhydride by the catalytic vapor-phase oxidation of o-xylene safely and stably even at an o-xylene concentration of more than 60 g/Nm$^3$, and a catalyst suitable for performing this process. Specifically, the inventors found that if the temperature of the gas at the inlet of the catalyst layer is maintained at not more than 150° C. and the concentration of oxygen in the starting gas is maintained at not more than 12% by volume, the danger of explosion is completely removed and therefore, any desired concentration of o-xylene can be employed, and that under these gas conditions, the gas completely falls outside the explosive range even at a site subsequent to the outlet of the reactor. Incident to this, the present inventors discovered a vanadium-titanium oxide type catalyst comprising anatase-type titanium oxide which is porous and has a particle diameter of about 0.4 to 0.7 micron and a specific surface area of 10 to 60 m$^2$/g as a catalyst which does not lose catalytic activity over a long period of time even within a low range of oxygen concentration.

The catalyst of this invention for the production of phthalic anhydride comprises a catalytically active material composed of 1 to 20 parts by weight as $V_2O_5$ of vanadium oxide, 99 to 80 parts by weight as $TiO_2$ of anatase-type titanium oxide being porous and having a particle diameter substantially of 0.4 to 0.7 micron and a specific surface area of 10 to 60 m$^2$/g, and per 100 parts by weight of the sum of these two components, 0.01 to 1 part by weight as $Nb_2O_5$ of niobium oxide, 0.05 to 1.2 parts by weight as an oxide of at least one ingredient selected from the group consisting of potassium, cesium, rubidium and thallium and 0.2 to 1.2 parts by weight as $P_2O_5$ of phosphorus, said catalytically active material being supported on a porous carrier having an alumina ($Al_2O_3$) content of not more than 10% by weight, a silicon carbide (SiC) content of at least 80% by weight, and an apparent porosity of at least 10%, wherein the total volume of pores having a diameter of 0.15 to 0.45 micron present in the layer of the catalytically active material on the carrier is at least 50%, preferably at least 70%, of that of pores having a diameter of not more than 10 microns present in said layer of the catalytically active material.

In one embodiment of this invention, phthalic anhydride is produced by passing a gaseous mixture containing naphthalene or o-xylene and air or another molecular oxygen-containing gas through a converter packed with the aforesaid catalyst, catalytically oxidizing naphthalene or o-xylene in the vapor phase at an elevated temperature, conducting the resulting phthalic anhydride-containing gas to a switch condenser, cooling the gas at a temperature higher than the dew point of water in the reaction product gas and recovering phthalic anhydride, and recycling a part of the exhaust gas from the condenser without removing water therefrom and then mixing it with the starting gas.

In another embodiment, a stacked catalyst layer composed of a layer of a "first-stage catalyst" and a layer of a "second-stage catalyst" is used. The first-stage catalyst comprises a catalytically active material composed of 1 to 20 parts by weight of $V_2O_5$, 99 to 80 parts by weight of anatase-type $TiO_2$ being porous and having a particle diameter substantially of 0.4 to 0.7 micron and a specific surface area of 10 to 60 m$^2$/g, and per 100 parts by weight of the sum of these two components, 0.01 to 1 part by weight of $Nb_2O_5$, 0.05 to 1.2 parts by weight of at least one ingredient selected from $K_2O$, $Cs_2O$, $Rb_2O$ and $Tl_2O$, and 0.2 to 0.4 part by weight of $P_2O_5$, and a carrier having a alumina content of not more than 10% by weight, a silicon carbide content of at least 80% by weight and an apparent porosity of at least 10%, supporting said catalytically active material thereon, wherein the total volume of pores having a diameter of 0.15 to 0.45 micron present in the layer of the catalytically active material on the carrier is at least 50%, preferably at least 70%, of that of pores having a diameter of not more than 10 microns present in said layer of the catalytically active material. This first-stage catalyst occupies 30 to 70% of the total height of the catalyst layer in the reaction tube from the inlet for the starting gas. The second-stage catalyst comprises a catalytically active material composed of 1 to 20 parts by weight of $V_2O_5$, 99 to 80 parts by weight of anatasetype $TiO_2$ being porous and having a particle diameter substantially of 0.4 to 0.7 micron and a specific surface area of 10 to 60 m$^2$/g, and per 100 parts by weight of the sum of these two components, 0.01 to 1 part by weight of $Nb_2O_5$, 0.05 to 1.2 parts by weight of at least one of $K_2O$, $Cs_2O$, $Rb_2O$ and $Tl_2O$, and 0.4 to 1.2 parts by weight of $P_2O_5$, and a carrier having an alumina content of not more than 10% by weight, a silicon carbide content of at least 80% by weight and an apparent porosity of at least 10% supporting said catalytically active material thereon, wherein the total volume of pores having a diameter of 0.15 to 0.45 micron present in the layer of the catalytically active material on the carrier is at least 50%, preferably at least 70%, of that of pores having a diameter of not more than 10 microns present in said layer of the catalytically active material. The second stage catalyst occupies 70 to 30% of the total height of the catalyst layer in the reaction tube from the outlet gas.

A combination of the use of this stacked catalyst layer with the recycling of the exhaust gas described above is the most preferred embodiment of this invention.

In the present invention, various processes such as (1), (2) and (3) described below can be used in recycling the exhaust gas to the converter.

(1) All of the exhaust gas from the condenser is passed through a catalytic combustion system packed with a platinum or palladium type catalyst, and then water is removed from the gas. A part of the resulting gas is recycled to the converter and mixed with the starting gas.

(2) All the exhaust gas from the condenser is sent to a tower adapted for recovering maleic anhydride. A part of the exhaust gas saturated with steam at the tower top temperature is recycled to the converter and mixed with the starting gas, and the remainder is conducted to a catalytic combustion system.

(3) A part of the exhaust gas from the condenser, without removing water from it, is recycled to the converter and mixed with the starting gas, and the remainder of the exhaust gas is conducted to a catalytic combustion system.

The process (3) is very simple and economical as compared with the processes (1) and (2). It is impossible however to apply a conventional $V_2O_5$-$TiO_2$ supported catalyst having a high selectivity to process (3). In the process (3), the concentration of steam at the inlet of the converter reaches 5 to 15% by volume although it varies according to the amount of o-xylene fed. Usually, in the production of an organic acid from a hydrocarbon compound by catalytic oxidation, the entraining of steam in the reaction gas is advantageous because steam acts as an accelerator for the desorption of the product from the catalyst surface and inhibits excessive oxidation reaction. The use of the conventional $V_2O_5$-$TiO_2$ type catalyst in the presence of steam is disadvantageous, however, because when naphthalene or o-xylene is oxidized with molecular oxygen in the presence of steam using the conventional $V_2O_5$-$TiO_2$ type supported catalyst, steam extremely accelerates the degradation of the catalyst as the time passes. For example, when the catalyst described in Example 1 of Japanese Patent Publication No. 4538/77 (U.S. Pat. No. 4,046,780) was packed to a height of 2.5 meters into a tube having an inside diameter of 20 mm, the tube was dipped in a molten salt bath at 370° C. and a gaseous mixture composed of 10% by volume of steam, 10% by volume of oxygen, 83 g/Nm$^3$ (the ratio of o-xylene/molecular oxygen) of o-xylene, and nitrogen was passed through the catalyst layer at a space velocity of 2,500 hr$^{-1}$, phthalic anhydride was obtained in a yield of more than 112% by weight in the early stage of reaction after the initiation, and the difference (abbreviated ΔT) between the temperature of the hot spot and the temperature of the molten salt was about 60° C. In about 2 months from the initiation of the reaction, however, ΔT decreased to 20° C., and the yield of phthalic anhydride decreased to 108% by weight.

The reason for this was extensively sought, and the following conclusions were obtained. When o-xylene is oxidized at an o-xylene/molecular oxygen-containing gas ratio of more than 80 g/Nm$^3$ at an oxygen concentration of as low as less than 12% by volume, both the concentration of o-xylene as a material to be oxidized and the concentration of oxygen exert a great load on the catalyst. To increase active sites in this case, a high loading catalyst could be produced by increasing the specific surface area of $TiO_2$ as one catalytically active substance. Specifically, the use of anatase-type $TiO_2$ having a specific surface area of at least 10 m$^2$/g, preferably about 15 to 40 m$^2$/g, i.e. anatase-type $TiO_2$ having a primary particle diameter of about 0.05 to 0.2 micron, is preferred. The use of this finely divided anatase-type $TiO_2$ as a material for catalyst is effective in obtaining a high loading catalyst, but has been found to suffer from the defect that the speed of degradation of the catalyst is high. Various physical analyses have shown that as the primary particle diameter of $TiO_2$ is smaller, the crystal growth of $TiO_2$ in the catalyst layer, especially at hot spots, increases, and the catalyst activity is decreased accordingly, and that when o-xylene is oxidized in the presence of steam, the steam accelerates the crystallization of $V_2O_5$ to needle-like crystals and aggravates the state of dispersion of $V_2O_5$ as an active site on the catalyst surface, and consequently, the activity of the catalyst is reduced.

Thus, $V_2O_5$-$TiO_2$ type supported catalysts for the production of phthalic anhydride by catalytic oxidation of o-xylene in the presence of steam under very high loading conditions would be industrially insignificant if the specific surface area of the anatase-type $TiO_2$ as a raw material is simply increased.

The present inventors therefore made various investigations in order to improve the durability of the catalyst under high loading conditions. These investigations have led to the discovery that the use of anatase-type $TiO_2$ being porous and having a particle diameter substantially of 0.4 to 0.7 micron and a specific surface area of 10 to 60 m$^2$/g, preferably 15 to 40 m$^2$/g, as a $TiO_2$ source leads to a marked improvement of the heat durability, especially steam resistance, of the catalyst, and therefore that the process (3) described hereinabove can be operated in the presence of the resulting catalyst. The catalyst in accordance with this invention operates even when steam is present only in an amount of about 0 to 5% by volume in the starting gas, and can be applied also to the processes (1) and (2) described hereinabove or to an ordinary one-pass process.

The catalyst of this invention consists basically of a catalytically active material composed of $V_2O_5$, anatase-type $TiO_2$ (to be referred to simply as $TiO_2$) being porous and having a particle diameter of 0.4 to 0.7 micron and a specific surface area of 10 to 60 m$^2$/g, $Nb_2O_5$, $P_2O_5$, and at least one of $K_2O$, $Cs_2O$, $Rb_2O$ and $Tl_2O$, and a porous carrier composed mainly of SiC supporting said catalytically active material thereon.

In the best mode of using the catalyst in an actual operation, the filling of the catalyst into a reaction tube is done in two layers (first-stage and second-stage), and the catalyst having a specified $P_2O_5$ content is filled in the starting gas inlet portion (first-stage), and the catalyst having a higher $P_2O_5$ content than the catalyst used in the starting gas inlet portion is filled in the product gas outlet portion (second-stage). According to this embodiment, the formation of hot spots in the catalyst layer is inhibited, and therefore, the high loading ability of the catalyst is increased.

The catalytically active material of the catalyst at the gas inlet portion (to be referred to as the first-stage catalyst) is composed of 1 to 20 parts by weight of $V_2O_5$, 99 to 80 parts by weight of $TiO_2$, and per 100 parts by weight of the sum of these two components, 0.01 to 1 part by weight of $Nb_2O_5$, 0.2 to 0.4 part by weight of $P_2O_5$, and 0.05 to 1.2 parts by weight of at least one of $K_2O$, $Cs_2O$, $Rb_2O$ and $Tl_2O$.

The catalytically active material of the catalyst at the gas outlet portion (to be referred to as the second-stage catalyst) is composed of 1 to 20 parts by weight of $V_2O_5$, 99 to 80 parts by weight of $TiO_2$, and per 100 parts by weight of the sum of these two components, 0.01 to 1.0 part by weight of $Nb_2O_5$, 0.4 to 1.2 parts by weight of $P_2O_5$, and 0.05 to 1.2 parts by weight of at least one of $K_2O$, $Cs_2O$, $Rb_2O$ and $Tl_2O$.

Anatase-type $TiO_2$ being porous and having a particle diameter of 0.4 to 0.7 micron and a specific surface area of 10 to 60 m$^2$/g, preferably 15 to 40 m$^2$/g, is used as a $TiO_2$ source. The use of anatase-type $TiO_2$ having a particle diameter of less than 0.4 micron and a specific surface area of 15 to 40 m$^2$/g is undesirable for the reason stated hereinabove. Anatase-type $TiO_2$ having the unique property of possessing a high specific surface area despite its large particle diameter is produced by mixing ilmenite with 70–80% conc. sulfuric acid, fllowing them to react fully with each other, diluting the reaction product with water to form an aqueous solution of titanium sulfate, adding iron fragments, reducing iron in the ilmenite, cooling the product to precipitate and separate ferric sulfate and to obtain an aqueous solution of highly pure titanium sulfate, blowing heated steam at 150° to 170° C. into the aqueous solution to hydrolyze it and precipitate hydrous titanium oxide, and calcining the titanium oxide at a temperature of 600° to 900° C. The specific surface area of 10 to 60 m$^2$/g corresponds to the particle diameter range of 0.05 to 0.20 micron of non-porous anatase-type $TiO_2$ (primary particles). Accordingly, the $TiO_2$ particles used in this invention are considered to be aggregated masses of such primary particles. The $TiO_2$ particles, however, can not be crushed by a mechanical means such as a hammer mill, and as far as this is concerned, they have such a strength as can be regarded as primary particles.

Depending upon the raw ilmenite ore, $TiO_2$ may include iron, zinc, aluminum, manganese, chromium, calcium, lead, etc. These incidental elements are not detrimental to the reaction if their total amount is less than 0.5% by weight based on $TiO_2$.

Raw materials for $V_2O_5$, $Nb_2O_5$, $P_2O_5$, $K_2O$, $Cs_2O$, $Rb_2O$ and $Tl_2O$ can be suitably selected from those which can change to oxides upon heating, such as the sulfates, ammonium salts, nitrates, organic acid salts, halides, and hydroxides of these metals.

A porous carrier composed mainly of SiC is used in the catalyst of this invention. Specifically, the porous carrier has an alumina content of not more than 10% by weight, preferably not more than 5% by weight, a silicon carbide content of at least 80% by weight, preferably at least 98% by weight, and an apparent porosity (to be referred to simply as porosity hereinbelow) of at least 10%, preferably 15 to 45%. A typical example of the carrier is the one obtained by self-bonding of a powder of SiC having a purity of 98% to adjust its porosity to 15-40%. The shape of the carrier is not particularly limited so long as its size is 2 to 15 mm in diameter. Spherical or circular-cylindrical carriers are suitable for handling.

The catalytically active material is supported on the carrier by a known conventional method. The simplest method comprises placing a fixed amount of the carrier in a rotary drum adapted to be externally heated, and spraying a liquid (e.g., slurry) containing the catalytically active material onto the carrier while maintaining the temperature at 200° to 300° C. The suitable amount of the catalytic material supported is 3 to 15 g/100 cc of carrier although varying depending upon the size of the carrier.

The titanium oxide used in the catalyst of this invention is essentially aggregated masses of primary particles although its mechanical strength is so high that it can be substantially regarded as primary particles. The particle diameter of the primary particles can be measured by a mercury penetration-type porosimeter. Accordingly, in order for both the first-stage and second-stage catalysts of this invention to meet the requirement that "the total volume of pores having a diameter of 0.15 to 0.45 micron present in the layer of the catalytically active material on the carrier is at least 50%, preferably at least 70%, of that of pores having a diameter of not more than 10 microns present in said layer of the catalytically active material", it is necessary to adjust the slurry concentration according to the particle diameter of the primary particles of titanium oxide, as described in the specification of Japanese Patent Publication No. 41036/74 (U.S. Pat. No. 3,962,846). When using porous titanium oxide consisting of primary particles having a particle diameter in the range of 0.005 to 0.05 micron, the concentration of the slurry is 5 to 25% by weight, preferably 10 to 20% by weight. When using porous titanium oxide consisting of primary particles having a particle diameter of 0.05 to 0.4 micron, the slurry concentration is 10 to 40% by weight, preferably 15 to 25% by weight.

The catalyst so obtained is then calcined at 300° to 600° C., preferably 350° to 550° C., for 2 to 10 hours in a current of air.

The catalyst and process in accordance with this invention are most suitable for the catalytic oxidation of o-xylene or naphthalene to form phthalic anhydride, but can also be applied to the catalytic oxidation of durene, acenaphthene, benzene, etc. to obtain the corresponding carboxylic acid anhydrides.

In use, the catalyst obtained in the above manner is packed into a tube having an inside diameter of 15 to 40 mm and a length of 1 to 5 meters. Preferably, the first-stage catalyst is packed so that it occupies 30 to 70% of the total height of the catalyst layer from the gas inlet portion, and the second-stage catalyst is packed so that it occupies the remainder (70 to 30% from the gas outlet portion) of the total height of the catalyst layer. If desired, the catalyst may be packed in three or more layers. In this case, the $P_2O_5$ content of the catalyst needs to be increased stepwise from the gas inlet portion to the gas outlet portion of the catalyst layer so that the aforesaid requirement of $P_2O_5$ content in the first-stage and second-stage catalysts is met.

In the stacked catalyst, the other components than $P_2O_5$ and their constituent porportions need not always to be the same for the individual layers, and can be varied as desired within the above-specified ranges.

The catalytic vapor-phase oxidation of o-xylene or naphthalene to form phthalic anhydride using the catalyst of this invention is usually carried out by mixing o-xylene or naphthalene with a molecular oxygen-containing gas composed of 5 to 21% by volume of oxygen, 0 to 15% by volume of steam, 0 to 3% by volume of carbon dioxide gas, 0 to 3% by volume of carbon monoxide and the balance being nitrogen, the concentration (to be abbreviated GC which stands for gas concentration) of the o-xylene or naphthalene being adjusted to 5 to 100 g per $Nm^3$ of molecular oxygen-containing gas, and passing the gaseous mixture over the catalyst layer at a temperature (the temperature of the heat transfer medium; to be abbreviated N.T.) of 300° to 400° C., preferably 330° to 380° C. and a pressure of normal atmospheric pressure to 10 atmospheres at a space velocity (to be abbreviated S.V.) of 1,000 to 6,000 $hr^{-1}$ (NTP).

Since the catalyst of this invention can catalyze the oxidation reaction of o-xylene or naphthalene under the aforesaid conditions, the present invention has made it possible to commercially operate a process for production of phthalic anhydride involving recycling exhaust gases which although being most economical, cannot be put into practice in the presence of conventional catalysts. In this process, the first-stage catalyst and the second-stage catalyst are stacked and filled into a multi-tube heat-exchanger converter, and heated to a predetermined temperature. First, o-xylene is passed through the catalyst layer at a G.C. of less than 40 g/$Nm^3$ of molecular oxygen-containing gas. At this time, the temperature of the starting gas is maintained at 100° to 120° C. The gas which has left the converter is passed through a multi-tube heat exchanger and is cooled to 160° C. The cooled gas is then conducted to a condenser adapted for recovery of phthalic anhydride which is filled with fin tubes, where phthalic anhydride is condensed. The temperature of the gas at the outlet of the condenser is maintained at more than the dew point of water according to the concentration of o-xylene. The gas which has left the condenser, without removing water from it, is partly recycled to the starting gas. It is mixed with air and again conducted to the converter together with o-xylene. Then, the amount of o-xylene fed is gradually increased, and more economically, the G.C. is increased to 80 to 90 g/$Nm^3$ of molecular oxygen-containing gas. At this time, the amount of the exhaust gas recycled is controlled to adjust the concentration of oxygen in the gas at the inlet portion of the converter to not more than 12% by volume. When the concentration of o-xylene is maintained at such a value, the gas at the inlet portion of the converter consists of 9 to 12% by volume of oxygen, 0.3 to 1.0% by volume of carbon monoxide, 1 to 4% by volume of carbon dioxide, 8 to 11% by volume of steam, 65 to 75% by volume of nitrogen and 1.7 to 1.9% by volume of o-xylene. At the exit of the condenser, the concentration of steam amounts to 15 to 18% by volume owing to the water generated at the converter. Accordingly, the temperature of the gas at the exit of the condenser should be maintained at a point above the dew point of water.

Intermediates such as phthalide or tolualdehyde to be recycled to the starting gas may be advantageous to the increase of the yield of phthalic anhydride, and are never disadvantageous to the catalyst. Since benzoic acid, an over-oxidized product to be recycled, is a monocarboxylic acid, it is very readily decomposed in the catalyst layer, and conveniently, it never builds up in the condenser for phthalic anhydride.

That part of the exhaust gas which is not recycled is sent to a catalytic combustion system, and after complete burning there, is released into the atmosphere.

Needless to say, the catalyst in accordance with this invention is also applicable to other processes for producing phthalic anhydride, for example an ordinary oxidation process in which the exhaust gas is not recycled; an oxidation process in which all the exhaust gas is introduced into a catalytic combustion system, and after water removal, a part of the exhaust gas is recycled to the starting gas; and an oxidation process in which all the exhaust gas is sent to a washing tower for the recovery of maleic anhydride, and a part of the exhaust gas from the washing tower is recycled to the starting gas.

The following examples illustrate the process of this invention in greater detail.

EXAMPLE 1

Heated steam at 175° C. was blown into an aqueous solution containing titanyl sulfate and sulfuric acid to form a precipitate of titanium hydroxide ($TiO_2 \cdot nH_2O$). The titanium hydroxide was washed with water and an acid, and further with water, and calcined at 800° C. for 4 hours. The calcined product was pulverized by a jet stream of air to obtain porous anatase-type $TiO_2$ having an average particle diameter of 0.5 micron and a BET specific surface area of 22 $m^2/g$.

To a solution of 1.8 kg of oxalic acid in 70 liters of deionized water were added 0.86 kg of ammonium meta-vanadate, 0.136 kg of niobium chloride, 0.067 kg of ammonium dihydrogen phosphate, 0.01 kg of potassium hydroxide and 0.0556 kg of cesium sulfate, and they were fully stirred. To the resulting aqueous solution was added 16 kg of $TiO_2$ produced as above, and they were fully emulsified for 40 minutes by an emulsifying machine to form a catalyst slurry.

One hundred and fifty (150) liters of self-bonded SiC having a porosity of 37% and a particle diameter of 5 mm as a carrier was placed in a stainless steel rotary oven adapted to be externally heated, and having a diameter of 2 meters and a length of 3 meters, and preheated to 200° to 250° C. While rotating the rotary oven, the slurry prepared as above was sprayed onto the carrier until the catalytically active material was deposited at a rate of 8 g/100 cc of carrier. The resulting catalyst was then calcined at 550° C. for 6 hours while passing air.

The catalytically active material had the following composition by weight.

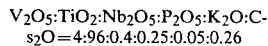
$s_2O = 4:96:0.4:0.25:0.05:0.26$

The pore size distribution of the catalyst prepared as above was measured by a mercury penetration-type porosimeter. It was found that the total volume of pores having a size of 0.15 to 0.45 micron was 88% of the total volume of pores having a size of not more than 10 microns (this is abbreviated as "the volume of pores having a size of 0.15 to 0.45 micron was 88%"). The resulting catalyst was designated as a first-stage catalyst.

In the above preparation of the catalyst slurry, the amount of ammonium dihydrogen phosphate was changed to 0.134 kg, and otherwise, the same procedure was repeated. There was obtained a catalyst in which the catalytically active material had the following composition by weight.

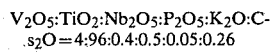
$s_2O = 4:96:0.4:0.5:0.05:0.26$

The volume of pores having a size of 0.15 to 0.45 micron was 86%. The resulting catalyst was designated as a second-stage catalyst.

First, the second-stage catalyst was packed to a height of 1.25 meters into a multi-tube heat exchanger converter consisting of 250 iron tubes having an inside diameter of 20 mm and a height of 3 meters whose inside surface was rust-proofed and treated with phosphoric acid. Then, the first-stage catalyst was packed into it to a height of 1.25 meters so that it was placed on top of the second-stage catalyst of a height of 1.25 meters. A molten salt as a heat transfer medium was circulated through the converter to maintain the temperature at 370° C.

A gaseous mixture of o-xylene and air preheated to 120° C. was introduced into the converter from its upper portion at a space velocity of 2,500 $hr^{-1}$ (NTP), and the concentration of the o-xylene was maintained at 40 $g/Nm^3$ of air. Then, an exhaust gas circulating blower was operated, and when the concentration of oxygen in the starting gas at the inlet of the converter reached 10%, the amount of the o-xylene fed was gradually increased, and finally to 83 $g/Nm^3$ of molecular oxygen-containing gas. At this time, the amount of the exhaust gas recycled was controlled with an increase in the amount of o-xylene fed so as to maintain the concentration of oxygen in the gas at the inlet of the converter at 10% by volume.

The gas which left the converter was cooled to 160° C. in a heat exchanger, and introduced into a switch condenser to crystallize phthalic anhydride. The exhaust gas left the condenser while maintaining the temperature of the outlet of the condenser at 77° C., and further passed through a conduit kept at 120° to 130° C. to mix 58% of it with air. The mixture was then introduced into the converter. The remainder of the exhaust gas (42%) was conducted to a catalytic combustion system, and after complete combustion, was released into the atmosphere. Under these conditions, the concentration of steam in the gas at the inlet of the converter reached about 9%. In a long-term operation over about a year, the reaction results shown in Table 1 were obtained.

TABLE 1

| Reaction time | N.T. (°C.) | S.V. ($hr^{-1}$) | G.C. ($g/Nm^3$) | Yield of phthalic anhydride (wt. %) | $\Delta T_1$(*) (°C.) | $\Delta T_2$(**) (°C.) |
|---|---|---|---|---|---|---|
| Initial stage | 370 | 2500 | 83 | 113.6 | 68 | 25 |
| 2 months | 370 | 2500 | 83 | 113.8 | 65 | 27 |
| 6 months | 372 | 2500 | 83 | 113.1 | 67 | 24 |
| 12 months | 375 | 2500 | 83 | 112.7 | 64 | 29 |

(*) $\Delta T_1 = \Delta T$ with the first-stage catalyst (the same definition applies to the following tables)
(**) $\Delta T_2 = \Delta T$ with the second-stage catalyst (the same definition applies to the following tables)

EXAMPLE 2

The titanium hydroxide obtained in Example 1 was calcined at 750° C. for 4 hours, and treated in the same way as in Example 1 to form porous anatase-type $TiO_2$ having an average particle diameter of 0.45 micron and a BET specific surface area of 28 $m^2/g$. By operating similarly to Example 1, catalysts having the following compositions were prepared by using the resulting anatase-type $TiO_2$ and a molded carrier composed of 2% by weight of alumina, 92% by weight of silicon carbide and the remainder being silica and having a porosity of 42% and a diameter of 5 mm.

First-stage catalyst $V_2O_5:TiO_2:Nb_2O_5:P_2O_5:Rb_2O = 15:85:0.5:0.35:0.40$ (by weight)

Second-stage catalyst $V_2O_5:TiO_2:Nb_2O_5:P_2O_5:Tl_2O = 8:92:0.5:1.0:0.8$ (by weight)

The volume of pores having a size of 0.15 to 0.45 micron was 83% in the first-stage catalyst, and 86% in the second-stage catalyst.

In a stainless steel tube having an inside diameter of 20 mm and a height of 3 meters, the first-stage catalyst was packed to a height of 0.8 meter, and the second-stage catalyst, to a height of 1.7 meters. A synthetic gas composed of 10% by volume of oxygen, 12% by volume of steam and 78% by volume of nitrogen was mixed with 80 $g/Nm^3$ of synthetic gas of o-xylene, and the gaseous mixture was passed throught the catalyst layers. The results obtained are shown in Table 2.

TABLE 2

| Reaction time | N.T. (°C.) | S.V. ($hr^{-1}$) | G.C. ($g/Nm^3$) | Yield of phthalic anhydride (wt. %) | $\Delta T_1$ (°C.) | $\Delta T_2$ (°C.) |
|---|---|---|---|---|---|---|
| Initial stage | 373 | 3000 | 80 | 112.8 | 71 | 21 |
| 3 months | 375 | 3000 | 80 | 112.5 | 68 | 24 |
| 6 months | 378 | 3000 | 80 | 112.4 | 70 | 20 |

EXAMPLE 3

The titanium hydroxide obtained in Example 1 was calcined at 850° C. for 6 hours, and treated by the same procedure as in Example 1 to afford porous anatase-type $TiO_2$ having a BET specific surface area of 17 $m^2/g$. Catalysts having the following compositions were prepared similarly to Example 1 by using the $TiO_2$ and a spherical powder of self-bonded SiC having a porosity of 35% as a carrier.

First-stage catalyst $V_2O_5:TiO_2:Nb_2O_5:P_2O_5:Cs_2) = 2:98:0.4:0.2:0.3$ (by weight)

Second-stage catalyst $V_2O_5:TiO_2:Nb_2O_5:P_2O_5:Cs_2O = 2:98:0.4:0.6:0.3$ (by weight)

The volume of pores having a size of 0.15 to 0.45 microns was 80% in the first-stage catalyst, and 84% in the second-stage catalyst.

Into a stainless steel tube having an inside diameter of 20 mm and a height of 5 meters, the first-stage catalyst was packed to a height of 1.8 meters, and the second-stage catalyst, to a height of 1.2 meters. A synthetic gas composed of 11% by volume of oxygen, 10% by volume of steam and 79% by volume of nitrogen was mixed with 85 $g/Nm^3$ of synthetic gas of o-xylene. The gaseous mixture was passed through the catalyst layer to react it. The results obtained are shown in Table 3.

TABLE 3

| Reaction time | N.T. (°C.) | S.V. ($hr^{-1}$) | G.C. ($g/Nm^3$) | Yield of phthalic anhydride (wt. %) | $\Delta T_1$ (°C.) | $\Delta T_2$ (°C.) |
|---|---|---|---|---|---|---|
| Initial stage | 370 | 2700 | 85 | 113.3 | 78 | 32 |
| 3 months | 370 | 2700 | 85 | 113.4 | 75 | 36 |
| 6 months | 372 | 2700 | 85 | 113.4 | 76 | 33 |

EXAMPLES 4 AND 5

Into a stainless steel tube having an inside diameter of 27 mm and a height of 3 meters, the first-stage catalyst obtained in Example 1 was packed to a height of 1.5 meters and the second-stage catalyst obtained in Example 1, to a height of 1.5 meters. Using air as an oxidizer, o-xylene was oxidized under the conditions shown in Table 4 using the catalyst layers obtained. The results are shown in Table 4.

TABLE 4

| | Reaction time | N.T. (°C.) | S.V. ($hr^{-1}$) | G.C. ($g/Nm^3$) | Yield of phthalic anhydride (wt. %) | $\Delta T_1$ (°C.) | $\Delta T_2$ (°C.) |
|---|---|---|---|---|---|---|---|
| | Initial stage | 360 | 3000 | 40 | 116.8 | 45 | 18 |
| Example 4 | 3 months | 360 | 3000 | 40 | 116.4 | 44 | 18 |
| | 6 months | 360 | 3000 | 40 | 116.5 | 44 | 19 |
| | Initial stage | 365 | 2700 | 60 | 114.1 | 68 | 28 |
| Example 5 | 3 months | 365 | 2700 | 60 | 113.8 | 66 | 28 |
| | 6 months | 365 | 2700 | 60 | 113.6 | 65 | 30 |

COMPARATIVE EXAMPLE 1

Ammonium titanium sulfate [$(NH_4)_2SO_4 \cdot TiOSO_4 \cdot H_2O$] was heat-treated at 900° C. for about 3 hours in accordance with the disclosure of Example 1 of the specification of Japanese Patent Publication No. 4538/77, and pulverized by a jet stream of air to afford finely divided anatase-type $TiO_2$ having a primary particle diameter of 0.25 micron and a specific surface area of 15 m²/g. Using a self-bonded SiC carrier having a particle diameter of 6 mm and a porosity of 35%, catalysts having the following compositions were prepared in the same way as in Example 1.

$V_2O_5:TiO_2:Nb_2O_5:P_2O_5:K_2O:$
$Na_2O=2:98:0.25:1.02:0.15:0.1$ (by weight)   (A)

$V_2O_5:TiO_2:Nb_2O_5:P_2O_5:K_2O:$
$Na_2O=2:98:0.25:1.3:0.15:0.1$ (by weight)   (B)

Into a stainless steel tube having an inside diameter of 20 mm and a height of 3 meters, the catalyst (A) was packed to a height of 1.25 m at the gas inlet portion, and the catalyst (B), to a height of 1.25 m at the gas outlet portion. Two such converters were provided. Oxidation of o-xylene was performed for a long period of time under the same loading conditions except that in one converter the content of steam in the inlet gas was adjusted to zero, and in the other converter, the content of steam in the inlet gas was adjusted to 10% by volume. The results are shown in Table 5.

TABLE 5

| Composition of the inlet gas | | Reaction time | N.T. (°C.) | S.V. (hr⁻¹) | G.C. (g/Nm³) | Yield of phthalic anhydride (wt. %) |
|---|---|---|---|---|---|---|
| O₂ | 10% | Initial stage | 375 | 2500 | 85 | 114.8 |
| H₂O | 0 | | | | | |
| o-Xylene | 85g/Nm³ | 3 months | 376 | 2500 | 85 | 114.4 |
| N₂ | balance | 6 months | 378 | 2500 | 85 | 114.1 |
| O₂ | 10% | Initial stage | 375 | 2500 | 85 | 114.9 |
| H₂O | 10% | | | | | |
| o-Xylene | 85g/Nm³ | 3 months | 381 | 2500 | 85 | 109.1 |
| N₂ | balance | 6 months | 387 | 2500 | 85 | 107.2 |

COMPARATIVE EXAMPLES 2 AND 3

Catalysts were prepared in the same way as in Examples 1 and 4 of the specification of Japanese Patent Publication No. 4538/77 except that a self-bonded SiC powder having a particle diameter of 5 mm and a porosity of 35% was used. Into a stainless steel tube having an inside diameter of 20 mm and a height of 3 meters, the first stage catalyst and the second-stage catalyst were packed to a height of 1.25 meters respectively. A gas composed of 10% by volume of oxygen, 10% by volume of steam and 80% by volume of nitrogen was mixed with 83 g/Nm³ of o-xylene, and the gaseous mixture was passed through the catalyst layer to react o-xylene. The results obtained are shown in Table 6.

TABLE 6

| Reaction time | | N.T. (°C.) | S.V. (hr⁻¹) | G.C. (g/Nm³) | Yield of phthalic anhydride (wt. %) | ΔT₁ (°C.) | ΔT₂ (°C.) |
|---|---|---|---|---|---|---|---|
| Comparative Example 2 (*) | Initial stage | 375 | 2500 | 83 | 113.7 | 67 | 21 |
| | 3 months | 381 | 2500 | 83 | 110.3 | 53 | 32 |
| | 6 months | 386 | 2500 | 83 | 108.1 | 38 | 43 |
| Comparative tive | Initial stage | 385 | 2500 | 83 | 113.3 | 64 | 19 |

TABLE 6-continued

| Reaction time | | N.T. (°C.) | S.V. (hr⁻¹) | G.C. (g/Nm³) | Yield of phthalic anhydride (wt. %) | ΔT₁ (°C.) | ΔT₂ (°C.) |
|---|---|---|---|---|---|---|---|
| Example 3(**) | 3 months | 393 | 2500 | 83 | 109.3 | 47 | 34 |
| | 6 months | 401 | 2500 | 83 | 107.3 | 32 | 51 |

(*) The catalysts in accordance with Example 1 of Japanese Patent Publication No. 4538/77.
(**) The catalysts in accordance with Example 4 of Japanese Patent Publication No. 4538/77.

EXAMPLE 6

The following two catalysts were prepared in accordance with Example 1 using the TiO₂ obtained in Example 1. The carrier used was self-bonded SiC having a particle diameter of 5 mm and a porosity of 35%.

| | | Volume (%) of pores having a size of 0.15–0.45 micron |
|---|---|---|
| A: | $V_2O_5:TiO_2:Nb_2O_5:Rb_2O:P_2O_5$ 4 : 98 : 0.6 : 0.35 : 0.3 | 85 |
| B: | $V_2O_5:TiO_2:Nb_2O_5:Rb_2O:P_2O_5$ 2 : 98 : 0.6 : 0.35 : 1.1 | 88 |

In a multi-tube heat exchanger converter consisting of twenty stainless steel tubes having an inside diameter of 20 mm and a height of 3.5 meters, the catalyst B was first packed to a height of 1.5 meters, and on top of it, the catalyst A was stacked to a height of 1.5 meters. A molten salt as a heat transfer medium was circulated through the converter to maintain the temperature at 365° C.

A gaseous mixture preheated to 120° C. of o-xylene and air was introduced into the converter from its upper portion at a space velocity of 2,000 hr⁻¹ (NTP). First, the concentration of o-xylene was maintained at 40 g/Nm³ of air. Then, an exhaust gas circulating blower was operated, and when the concentration of oxygen in the starting gas reached 11% by volume, the concentration of o-xylene was increased gradually, and finally to 100 g/Nm³ of molecular oxygen-containing gas. The amount of the exhaust gas recycled was controlled with an increase of in the amount of o-xylene fed so that the concentration of oxygen in the starting gas was maintained at 11% by volume.

The gas which left the converter was cooled to 160° C. in a heat exchanger, and introduced into a switch condenser to crystallize phthalic anhydride. At this time, about 33% of the total phthalic anhydride formed was recovered in the liquid state. The exhaust gas was withdrawn from the condenser while maintaining the temperature of the outlet of the condenser at 78° C., and was conducted to a tower for recovering maleic anhydride. About 35% of the exhaust gas containing steam saturated at a tower top temperature of 35° C. was recycled to the starting gas. The remainder was released into the atmosphere through the complete-combustion system. Under these conditions, the concentration of steam in the starting gas was about 3%. In a long-term operation over about 6 months, the reaction results shown in Table 7 were obtained.

TABLE 7

| Reaction time | N.T. (°C.) | S.V. (hr$^{-1}$) | G.C. (g/Nm$^3$) | Yield of phthalic anhydride (wt. %) | $\Delta T_1$ (°C.) | $\Delta T_2$ (°C.) |
| --- | --- | --- | --- | --- | --- | --- |
| Initial stage | 365 | 2000 | 100 | 111.9 | 65 | 35 |
| 3 months | 367 | 2000 | 100 | 111.8 | 63 | 37 |
| 6 months | 370 | 2000 | 100 | 111.5 | 60 | 40 |

EXAMPLE 7

The same hydrous titanium oxide as obtained in Example 1 was calcined at 700° C. for 5 hours in a current of air, and pulverized by a jet of air stream to obtain porous TiO$_2$ having a particle diameter of 0.45 micron and a specific surface area of 33 m$^2$/g.

The following two catalysts were prepared in accordance with Example 1 using a self-bonded SiC carrier having a particle diameter of 5 mm and a porosity of 35%.

|   |   | Volume of pores having a size of 0.15–0.45 microns |
| --- | --- | --- |
| A: | V$_2$O$_5$:TiO$_2$:Nb$_2$O$_5$:Rb$_2$O:P$_2$O$_5$<br>15 : 85 : 1.0 : 0.28 : 0.35 | 80 |
| B: | V$_2$O$_5$:TiO$_2$:Nb$_2$O$_5$:Rb$_2$O:P$_2$O$_5$<br>15 : 85 : 1.0 : 0.28 : 1.0 | 82 |

Into the same converter as in Example 6, the catalyst B was first packed to a height of 1 meter, and then the catalyst A was stacked to a height of 1.5 meters. The temperature of the heat transfer medium was maintained at 360° C. A gaseous mixture of naphthalene and air preheated to 140° C. was introduced into the converter from its upper portion at a space velocity of 3,000 hr$^{-1}$. The concentration of naphthalene was first maintained at 40 g/Nm$^3$ of air, and then by the same operation as in Example 6, the concentration of a naphthalene was finally increased to 60 g/Nm$^3$ of molecular oxygen-containing gas.

The tower top temperature of a tower for recovery of maleic anhydride and quinone was maintained at 35° C. The ratio of the exhaust gas which was recycled was 66% (the concentration of oxygen in the gas at the inlet portion of the converter was 11% by volume), and the concentration of steam in the gas at the inlet of the reactor was about 4%.

The results of the reaction are shown in Table 8.

TABLE 8

| Reaction time | N.T. (°C.) | S.V. (hr$^{-1}$) | G.C. (g/Nm$^3$) | Yield of phthalic anhydride (wt. %) | $\Delta T_1$ (°C.) | $\Delta T_2$ (°C.) |
| --- | --- | --- | --- | --- | --- | --- |
| Initial stage | 360 | 3000 | 60 | 103.2 | 60 | 32 |
| 2 months | 364 | 3000 | 60 | 102.9 | 56 | 35 |
| 4 months | 366 | 3000 | 60 | 102.7 | 54 | 36 |
| 6 months | 368 | 3000 | 60 | 102.6 | 53 | 36 |

What we claim is:

1. A process for producing phthalic anhydride, which comprises packing a catalyst into a multitude fixed bed converter, said catalyst comprising a catalytically active material composed of 1 to 20 parts by weight as V$_2$O$_5$ of vanadium oxide, 99 to 80 parts by weight of anatase-type titanium oxide being porous and having a particle diameter substantially of 0.4 to 0.7 micron and a specific surface area of 10 to 60 m$^2$/g, and per 100 parts by weight of the sum of said two components, 0.01 to 1 part by weight as Nb$_2$O$_5$ of niobium oxide, 0.05 to 1.2 parts by weight as an oxide of at least one ingredient selected from the group consisting of potassium, cesium, rubidium and thallium, and 0.2 to 1.2 parts by weight as P$_2$O$_5$ of phosphorus, and a porous carrier having an alumina content of not more than 10% by weight, a silicon carbide content of at least 80% by weight and an apparent porosity of at least 10% supporting said catalytically active material thereon in an amount of about 3 to 15 grams per 100 cubic centimeters of said carrier, wherein the total volume of pores having a diameter of 0.15 to 0.45 micron present in the layer of the catalytically active material on the carrier is at least 50% of that of pores having a diameter of not more than 10 microns present in said layer of the catalytically active material; and passing a starting gas comprising o-xylene or naphthalene and oxygen or a molecular oxygen-containing gas, said starting gas having a temperature of not more than 150° C. at the inlet of the converter and a concentration of oxygen of not more than 12% by volume, through the catalyst layer at a temperture of 300° to 450° C., thereby catalytically oxidizing the o-xylene or naphthalene.

2. A process for producing phthalic anhydride, which comprises packaging a first-stage catalyst into a multitube fixed bed reactor to a height of 30 to 70% of the total height of the catalyst layer from the gas inlet side and a second-stage catalyst, which is the same as the first-stage catalyst except that its phosphorus content is 0.4 to 1.2% by weight as P$_2$O$_5$, to a height of 70 to 30% of the total height of the catalyst layer of the converter from the gas outlet side, said first-stage catalyst comprising a catalytically active material composed of 1 to 20 parts by weight as V$_2$O$_5$ of vanadium oxide, 99 to 80 parts by weight of anatase-type titanium oxide being porous and having a particle diameter substantially of 0.4 to 0.7 micron and a specific surface area of 10 to 60 m$^2$/g, and per 100 parts by weight of the sum of said two components, 0.01 to 1 part by weight as Nb$_2$O$_5$ of niobium oxide, 0.05 to 1.2 parts by weight as an oxide of at least one ingredient selected from the group consisting of potassium, cesium, rubidium and thallium and 0.2 to 0.4 parts by weight as P$_2$O$_5$ of phosphorus, and a porous carrier having an alumina content of not more than 10% by weight, a silicon carbide content of at least 80% by weight and an apparent porosity of at least 10% supporting said catalytically active material thereon in an amount of about 3 to 15 grams per 100 cubic centimeters of said carrier, wherein the total volume of pores having a diameter of 0.15 to 0.45 micron present in the layer of the catalytically active material on the carrier is at least 50% of that of pores having a diameter of not more than 10 microns present in said layer of the catalytically active material; and passing a starting gas comprising o-xylene or naphthalene and oxygen or a molecular oxygen-containing gas, said starting gas having a temperature of not more than 150° C. at the inlet of the converter and a concentration of oxygen of not more than 12% by volume, through the stacked catalyst layers at a temperature of 300° to 450° C., thereby catalytically oxidizing the o-xylene or naphthalene.

3. The process of claim 1 or 2 which further comprises cooling the product gas from the multitube fixed bed converter by a heat exchanger, conducting the cooled product gas to a switch condenser adapted for recovery of phthalic anhydride, cooling the product gas therein at a temperature higher than the dew point of water in the product gas and recovering phthalic anhydride, recycling a part of the exhaust gas from the condenser to the converter and mixing it with the starting gas for further reaction, and either discharging the remainder of the exhaust gas directly, or conducting it to a catalytic combustion system and completely burning it therein.

4. The process of claim 1 or 2 which further comprises cooling the product gas from the multitude fixed bed converter by a heat exchanger, conducting the cooled product gas to a switch condenser adapted for recovery of phthalic anhydride, cooling the product gas therein at a temperature higher than the dew point of water in the product gas and recovering phthalic anhydride, sending all of the exhaust gas from the condenser to a tower adapted for recovery of maleic anhydride and phthalic anhydride, recycling a part of the exhaust gas saturated with steam at the temperature of the tower top to the converter and mixing it with the starting gas for further reaction, and either discharging the remainder of the exhaust gas directly, or conducting it to a catalytic combustion system and burning it completely.

5. The process of claim 1 or 2 which further comprises cooling the product gas from the multitube fixed bed converter by a heat exchanger, conducting the cooled product gas to a switch condenser adapted for recovery of phthalic anhydride, cooling the product gas therein at a temperature higher than the dew point of water in the product gas and recovering phthalic anhydride, conducting all of the exhaust gas from the condenser to a catalytic combustion system and burning it completely, conducting the burned gas to a water removing device and removing moisture therefrom, recycling a part of the resulting gas to the converter and mixing it with the starting gas for further reaction, and discharging the remainder of the exhaust gas out of the system.

6. The process of any one of claims 1 or 2 wherein said carrier has a silicon carbide content of 98% and a porosity of at least 10%.

7. The process of any one of claims 1 or 2 wherein the starting gas contains the o-xylene or naphthalene in a concentration of 60 to 100 g/Nm$^3$.

8. The process of claim 3 wherein said carrier has a silicon carbide content of 98% and a porosity of at least 10%.

9. The process of claim 4 wherein said carrier has a silicon carbide content of 98% and a porosity of at least 10%.

10. The process of claim 5 wherein said carrier has a silicon carbide content of 98% and a porosity of at least 10%.

11. The process of claim 3 wherein the starting gas contains the o-xylene or napthalene in a concentration of 60 to 100 g/Nm$^3$.

12. The process of claim 4 wherein the starting gas contains the o-xylene or naphthalene in a concentration of 60 to 100 g/Nm$^3$.

13. The process of claim 5 wherein the starting gas contains the o-xylene or naphthalene in a concentration of 60 to 100 g/Nm$^3$.

14. The process of claim 6 wherein the starting gas contains the o-xylene or naphthalene in a concentration of 60 to 100 g/Nm$^3$.

15. The process of claims 1 or 2 wherein the starting was comprises o-xylene or naphthalene and a molecular oxygen-containing gas composed of 5 to 21% by volume of oxygen, 0 to 15% by volume of steam, 0 to 3% by volume of carbon dioxide, 0 to 3% by volume of carbon monoxide, and the balance being nitrogen, the concentration of the o-xylene or naphthalene being in the range of from 5 to 100 g/Nm$^3$ of said molecular oxygen-containing gas.

* * * * *

UNITED STATES PATENT AND TRADEMARK OFFICE
CERTIFICATE OF CORRECTION

PATENT NO. : 4,284,571
DATED : August 18, 1981
INVENTOR(S) : Sato, et al.

It is certified that error appears in the above—identified patent and that said Letters Patent is hereby corrected as shown below:

Claim 15, line 2, delete "was" and insert -- gas --

Claim 1, line 2, delete "multitude" and insert -- multitube --

Claim 4, line 2, delete "multitude" and insert -- multitube --.

Signed and Sealed this

Twentieth Day of October 1981

[SEAL]

Attest:

Attesting Officer

GERALD J. MOSSINGHOFF

Commissioner of Patents and Trademarks